United States Patent
Lin et al.

(10) Patent No.: US 11,786,393 B2
(45) Date of Patent: Oct. 17, 2023

(54) OSTOMY POUCHING DEVICE

(71) Applicants: Chih-Hao Lin, Taipei (TW);
Wan-Chen Shen, Taipei (TW);
Wei-Ting Shih, Taoyuan (TW)

(72) Inventors: Chih-Hao Lin, Taipei (TW);
Wan-Chen Shen, Taipei (TW);
Wei-Ting Shih, Taoyuan (TW)

(*) Notice: Subject to any disclaimer, the term of this patent is extended or adjusted under 35 U.S.C. 154(b) by 607 days.

(21) Appl. No.: 16/038,164

(22) Filed: Jul. 17, 2018

(65) Prior Publication Data

US 2019/0015241 A1 Jan. 17, 2019

Related U.S. Application Data

(60) Provisional application No. 62/533,168, filed on Jul. 17, 2017.

(51) Int. Cl.
*A61F 5/44* (2006.01)
*A61F 5/445* (2006.01)
(Continued)

(52) U.S. Cl.
CPC ............ *A61F 5/441* (2013.01); *A61F 5/4404* (2013.01); *A61F 5/4405* (2013.01); *A61F 5/445* (2013.01);
(Continued)

(58) Field of Classification Search
CPC ...... A61F 5/441; A61F 5/4404; A61F 5/4405; A61F 5/4407; A61F 5/445; A61F 5/449; A61F 2005/4455; A61F 2250/0003; A61F 5/44; B29L 2009/00; B29L 2022/022; A61B 17/11; A61B 2017/1103; A61B 2017/1125; A61B 17/1114; A61B 2017/1121; A61B 17/12022;
(Continued)

(56) References Cited

U.S. PATENT DOCUMENTS 2,905,270 A * 9/1959 Jackson .................. F16N 27/00
184/7.4
3,828,782 A * 8/1974 Polin ...................... A61F 5/445
604/103.03

(Continued)

FOREIGN PATENT DOCUMENTS

EP 2211728 B1 12/2015
WO WO2016/008981 1/2016

OTHER PUBLICATIONS

PCT/US2018/042570 Notification of Transmittal of the International Search Report and the Written Opinion of the International Searching Authority, or the Declaration.
(Continued)

*Primary Examiner* — Erich G Herbermann
*Assistant Examiner* — Alessandro R Del Priore
(74) *Attorney, Agent, or Firm* — Rita H. Lin

(57) ABSTRACT

An ostomy pouching device for the removal of biological waste from a patient. An embodiment of an ostomy pouching device includes an outer container housing an inner bag for receiving waste from a patient's bowel. The device includes a bowel connector to connect the bowel to the inner bag. The outer container includes an air exit aperture through which air may exit the container as it is displaced as the inner bag expands, and a gas tunnel for removing gas from the inner bag.

37 Claims, 9 Drawing Sheets

(51) Int. Cl.
*A61F 5/449* (2006.01)
*A61F 5/441* (2006.01)

(52) U.S. Cl.
CPC ............ *A61F 5/4407* (2013.01); *A61F 5/449* (2013.01); *A61F 2005/4455* (2013.01)

(58) Field of Classification Search
CPC ........ A61B 17/12027; A61B 17/12031; A61B 17/1204; A61B 17/12045; A61B 17/12036
See application file for complete search history.

(56) References Cited

U.S. PATENT DOCUMENTS

| | | | |
|---|---|---|---|
| 3,937,224 A * | 2/1976 | Uecker | A61F 5/445 |
| | | | 604/277 |
| 4,786,283 A * | 11/1988 | Andersson | A61F 5/448 |
| | | | 604/328 |
| 4,826,495 A | 5/1989 | Petersen | |
| 4,938,750 A | 7/1990 | Leise, Jr. | |
| 5,591,144 A | 1/1997 | Smith et al. | |
| 5,690,622 A * | 11/1997 | Smith | A61F 5/441 |
| | | | 604/333 |
| 5,690,623 A | 11/1997 | Lenz et al. | |
| 5,785,695 A | 7/1998 | Sato et al. | |
| 9,204,990 B1 * | 12/2015 | Berven | A61F 5/445 |
| 9,314,365 B2 | 4/2016 | Hanuka et al. | |
| 9,629,743 B2 | 4/2017 | Grum-Schwensen | |
| 9,928,341 B2 | 3/2018 | Angelides | |
| 9,993,364 B2 | 6/2018 | Fernandez et al. | |
| 10,004,629 B1 | 6/2018 | Carrero | |
| 2003/0220621 A1 * | 11/2003 | Arkinstall | A61F 5/445 |
| | | | 604/335 |
| 2008/0262449 A1 | 10/2008 | Shah et al. | |
| 2011/0015475 A1 | 1/2011 | Hanuka et al. | |
| 2011/0040231 A1 * | 2/2011 | Gregory | A61F 5/445 |
| | | | 604/8 |
| 2011/0092929 A1 | 4/2011 | Weig | |
| 2011/0190584 A1 * | 8/2011 | Sugahara | A61B 17/12109 |
| | | | 600/116 |
| 2011/0196323 A1 * | 8/2011 | Gill | A61F 5/4405 |
| | | | 604/333 |
| 2012/0136324 A1 * | 5/2012 | Hanuka | A61F 5/441 |
| | | | 604/318 |
| 2012/0232505 A1 | 9/2012 | Eskaros et al. | |
| 2012/0234485 A1 | 9/2012 | Smith et al. | |
| 2013/0231523 A1 * | 9/2013 | Forsell | A61N 1/36007 |
| | | | 600/30 |
| 2015/0265455 A1 * | 9/2015 | Fernandez | A61F 5/448 |
| | | | 604/342 |
| 2015/0305916 A1 | 10/2015 | Hanuka et al. | |
| 2015/0320585 A1 | 11/2015 | Fattman et al. | |
| 2016/0235581 A1 | 8/2016 | Keleny et al. | |

OTHER PUBLICATIONS

Supplementary Partial European Search Report.

\* cited by examiner

OSTOMY POUCHING DEVICE

CROSS REFERENCE TO RELATED APPLICATIONS

The application claims the benefit of U.S. Provisional Application No. 62/533,168, filed on Jul. 17, 2017, which is incorporated by reference herein in its entirety.

FIELD OF INVENTION

The invention is related to an ostomy pouching device.

BACKGROUND OF THE INVENTION

An ostomy operation is often necessary as part of treatment to various medical conditions, such as surgery to remove cancerous growth, which requires the removal of part or all of a patient's bowels, such as the small or large intestine. After the surgery, if the bowels are not reattached, the waste from the bowels, such as urine and feces, are usually removed from the body through an artificial opening in the patient's abdominal wall.

Methods presently available to collect such waste often involve the use of a reservoir. A conventional method for collecting and disposing of waste calls for using an ostomy bag connected to the bowel. The bag usually must be emptied and cleaned frequently, usually every several hours. The ostomy bag is usually positioned outside of the abdomen, and often taped to the patient's skin.

There are several drawbacks associated with the conventional methods. First, the connection between the stoma and the ostomy bag are often not 100% secure. Leakage and odor are common issues faced by patients. The stoma often requires special care to prevent irritation and infection. Similarly, the skin to which the ostomy bag is adhered becomes irritated as well.

Furthermore, using and wearing an ostomy bag may create major quality of life issues. The fear of embarrassment of possible leakage and odor often lead to self-imposed social isolation, as patients limit their physical and social activities. This may lead to depression and other psychological suffering.

Accordingly, it is desirable to provide an improved device and method that overcomes drawbacks and inadequacies of known methods and devices.

SUMMARY OF THE INVENTIONS

Generally speaking, in accordance with an embodiment of the invention, an ostomy pouching device includes a container that may be implanted into the body, between the skin and the abdominal muscle. The container includes an aperture for connecting to the bowel for receiving waste therefrom, and an aperture for removing the contents of the container.

An embodiment of the invention provides an inner bag within the container into which the waste enters from the bowel. The air in the container is displaced and exits the container as the inner bag expands with waste entering the inner bag.

Another embodiment of the invention provides a container having a gas tunnel. The gas tunnel includes a gas entrance through which gas from within the container or inner bag enters the gas tunnel, and a gas exit through which the gas exits the container.

Yet another embodiment of the invention is directed to a container constructed to permit the removal of an inner bag without removing the container.

Another embodiment of the invention provides a branched bowel connector which permits the reconnection of the bowels. The branched bowel connector includes a stopper which prevents contents from the upstream end of the bowel to enter the downstream end of the bowel.

Still other objects and advantages of the invention will in part be obvious and will in part be apparent from the specification. Other features and advantages of this invention will become apparent in the following detailed description of exemplary embodiments of this invention with reference to the accompanying drawings.

BRIEF DESCRIPTION OF THE DRAWINGS

For a fuller understanding of the invention, reference is made to the following description taken in connection with the accompanying drawing, in which.

DETAILED DESCRIPTION OF THE PREFERRED EMBODIMENTS

Figure 1:
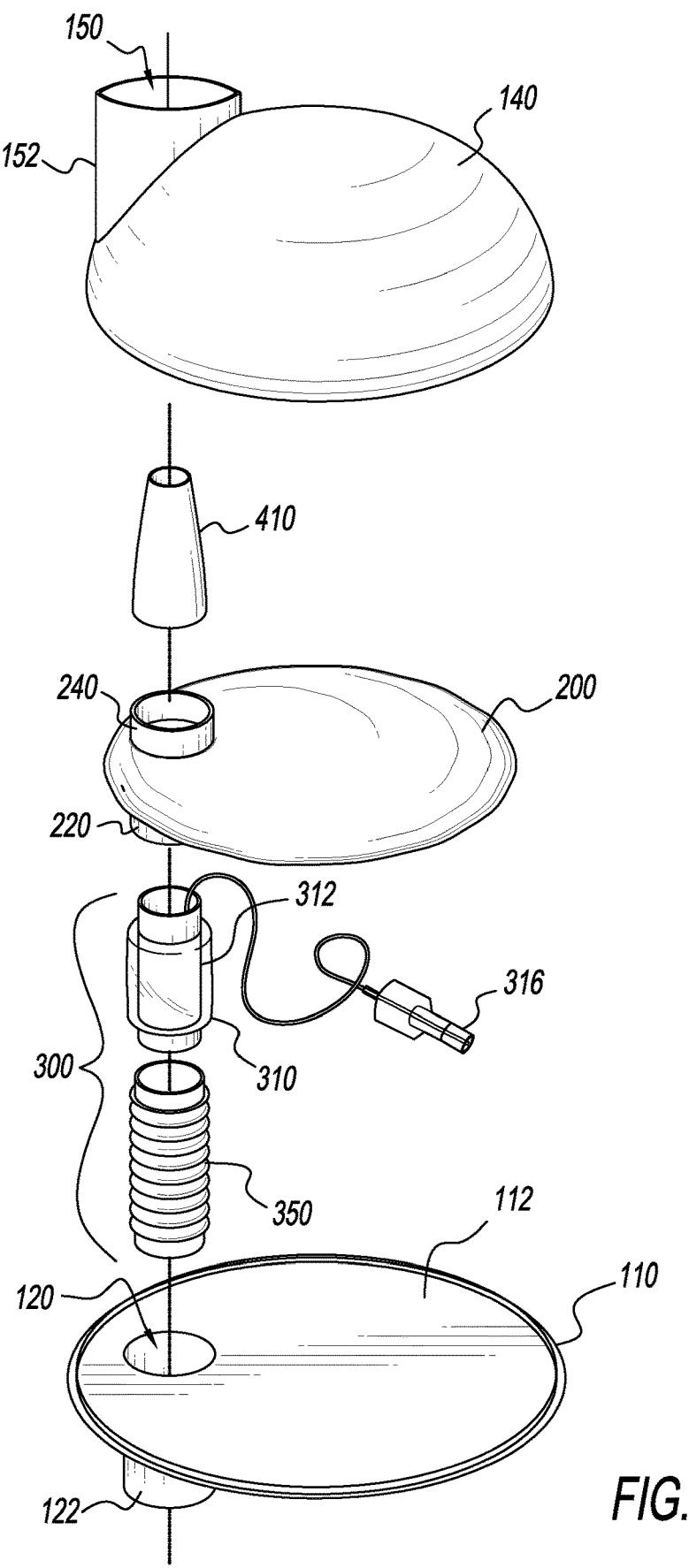
FIG. 1 is an exploded perspective view of an ostomy pouching device in accordance with an embodiment of the invention.

The invention generally is directed to an ostomy pouching device 1 comprising an outer container referred to herein generally as "container," and preferably an inner waste collection pouch referred to herein generally as "inner bag," for placement within the container. The container may be located either inside or outside of the body. Preferably, the container is implanted between the skin and the muscle, preferably the abdominal muscle. The term "container" is used herein generally to refer to any receptacle capable of housing a pouch therein, by way of non-limiting example, a shell having a defined shape, or a pouch that is flat when empty and expands as it is filled.

Reference is made to FIGS. 1-11, wherein certain embodiments of the invention are illustrated. In the embodiments illustrated, the device 1 includes a container 100 having a base 110, an upper member 140, and a container cavity 160. Base 110 has a base wall 112, which is generally flat and smooth. Base wall 112 includes a base aperture 120, and preferably a base tunnel 122 defining base aperture 120, which is designed to be connected to the bowel of the user, such as a patient. Base wall 112 includes an inner wall surface which faces the upper member 140 when base 110 and upper member 140 are assembled. Base wall 112 further includes an outer wall surface which faces the user's bowels when implanted in the user's body. Whereas the embodiments of base 110, 110a illustrated are shown as having a flat surface, it is to be understood that other shapes are contemplated. For example, base 100 may have a curved or wavy shape without deviating from the scope of the invention.

Upper member 140 preferably has a bulbous shape, for example, a dome shape as illustrated. An upper aperture 150 is defined by an upper tunnel 152, through which the contents of container 100, more preferably the contents of an inner bag 200 located within container 100, may be removed. Preferably, an air exit aperture 154 is provided through which air or other gas within container cavity 160 can exit container 100. In the embodiments shown, air exit aperture 154 is located proximate or within upper tunnel 152, and is open at all times, permitting air from container cavity 160 to exit. Air exit aperture 154 may include a valve or other mechanism to allow manual release of air from container cavity 160.

Upper member 140 may also include a gas tunnel 142 through which gas may flow from within container 100 and/or inner bag 200 to a gas exit 144. Gas exit 144 may be located proximate or incorporated into upper tunnel 152. In the embodiment shown in FIG. 3, gas exit 144 is integrated into upper tunnel 152. Gas tunnel 142 may be integral to upper member 140, built into the wall of upper member 140, or it may be a separate element, such as a tube. Furthermore, whereas the illustrations show a single gas tunnel 142, a plurality of gas tunnels 142 may be provided. The gas tunnel entrance 146 is preferably located above base aperture 120 and base tunnel 122, which connects to the bowel, and more preferably above upper aperture 150 and upper tunnel 152, when the user having device 1 implanted or otherwise connected to his body is standing. Since heavier liquids and solids would fall downward due to gravity, and the lighter gas would rise up, the gas preferably separates from the liquids and solids, and enters gas tunnel 142. Gas tunnel entrance 146 may include a valve to restrict and prevent solid and/or liquid from entering gas tunnel 142. Gas exit 144 may alternatively connect to a separate container. Gas exit 144 may always stay open or include a valve or other mechanism to selectively release gas from within gas tunnel 142. Preferably, gas exit 144 may be opened independently of external tube 410 or upper aperture 150.

Container 100 may be manufactured from a variety of material. A preferred material is silicone. Other non-limiting examples include nylon, polypropylene, and titanium. Preferably, at least for a device 1 being implanted in a user's body, container 100 is made of a material stable as an implant. Furthermore, container 100 is preferably flexible enough to bend inward and squeeze an inner bag 200 therein when pressured is applied inward onto container 100, for example, when emptying inner bag 200.

In accordance with a preferred embodiment, an inner bag 200 is located within container 100. Preferably, inner bag 200 is collapsible, expanding as contents enter it. Preferably, inner bag is produced from vinyl plastics, more preferably PVC (polyvinyl chloride). Other materials are contemplated without deviating from the scope of the invention. As inner bag 200 is filled, for example, with waste such as urine and feces, the air within container cavity 160 is displaced, and exits container 100 through air exit aperture 154. In the embodiments shown, inner bag 200 includes at least two apertures, each connected to a connecting element. For example, a first aperture to connect to a bowel connecting element 220 arranged to connect to a bowel connector 300 to connect to the user's bowel through which contents enter inner bag 200 from the user's bowels, and a second aperture to connect to an external connecting element 240 arranged to connect to a tube through which the contents of inner bag 200 are removed. A gas exit 260 may also be provided, through which gas exits inner bag 200. Preferably, gas exit 260 is connected to gas tunnel entrance 146 of container 100, so that gas from within inner bag 200 exits inner bag 200 into gas tunnel 142 and exits container 100 through gas exit 144.

Alternatively, inner bag 200 may be made of a water resistant but gas permeable material, or include a water resistant but gas permeable portion, permitting gas to exit therethrough while keeping the liquid and solid inside. The gas may exit inner bag 200 into container cavity 160 and exit through air exit aperture 154. This gas permeable portion may be provided in lieu of an opening to connect directly to the gas tunnel 142, or in combination thereof. Gas tunnel entrance 146, gas exit 144, gas tunnel 142, and/or upper aperture 150 may include a filter or smell absorbing or filtering component.

Gas often occupies a substantial volume of an ostomy pouch, precious volume that may otherwise be occupied by solid or liquid waste. For example, the average small intestine passes between 500 to 1000 ml of fluid a day, and between 500 to 1800 ml of gas. By permitting the removal of gas from inner bag 200 independently of solid or liquid waste, the device 1 may prolong the use of device 1 before requiring emptying thereof.

The device 1 preferably includes a bowel connector 300 to connect inner bag 200 and container 100 to the user's bowel. In the embodiments shown, bowel connector 300 extends through base tunnel 122 of container 100. Reference is made to FIGS. 4-7 illustrating a preferred embodiment of bowel connector 300. Bowel connector 300 includes an inner tube 310 and outer tube 350. An outer member may be provided to wrap around outer tube 350 to create an anti-adhesion membrane. Bowel connector 300 may be integrated with bowel connection 220 and base tunnel 122, preferably so that there is no gap between the bowel and base tunnel 122. For example, inner tube 310 may be integrated with inner bag 200, and outer tube 350 may be integrated with base 110, preferably at base tunnel 122. Alternatively, as shown in the figures, inner tube 310 may be a separate piece that connects to bowel connection 220 of inner bag 200, preferably at bowel connection 220. Likewise, outer tube 350 may be a separate piece that connects to base 110 through base tunnel 122 or connects to base tunnel 122.

Figure 4:
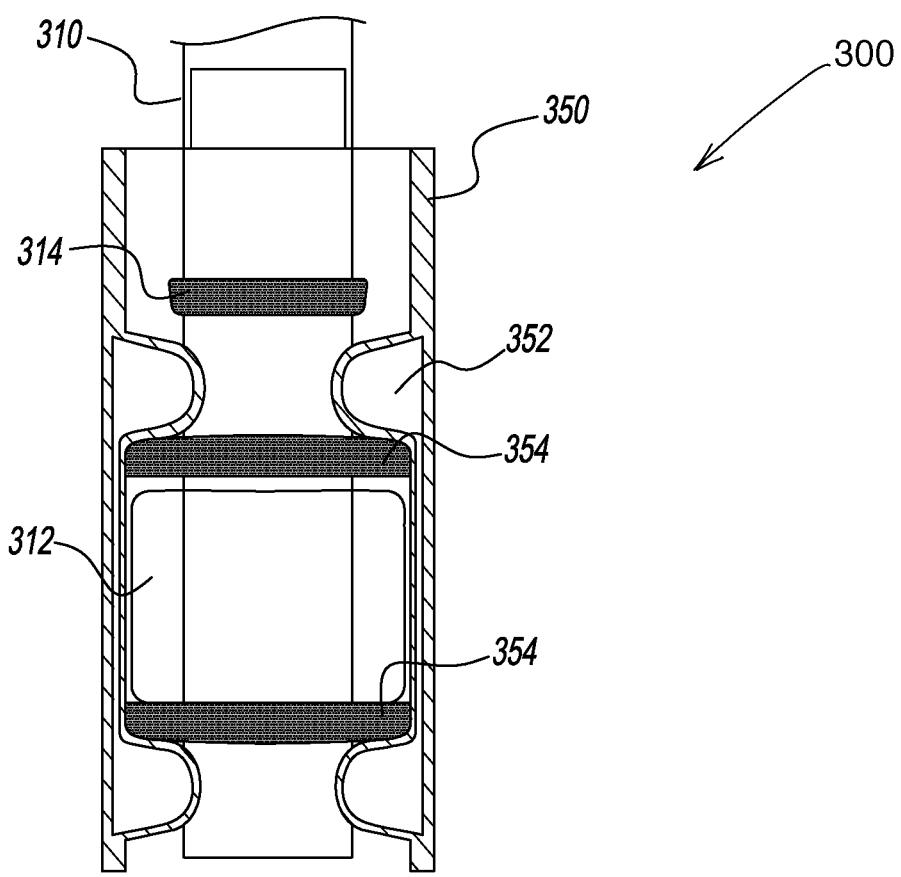
FIG. 4 is a cross-sectional view of a bowel connector in accordance with an embodiment of the invention having an inflated inner tube balloon and an inflated outer tube balloon.
Figure 5:
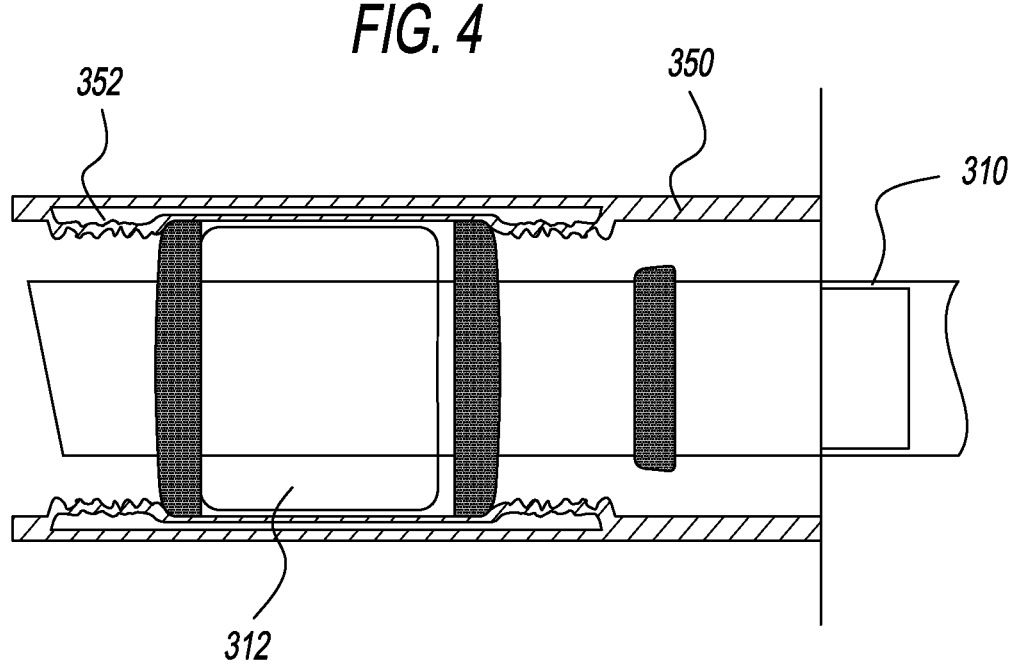
FIG. 5 is a cross-sectional view of the bowel connector of FIG. 4 having a deflated outer tube balloon.
Figure 6:
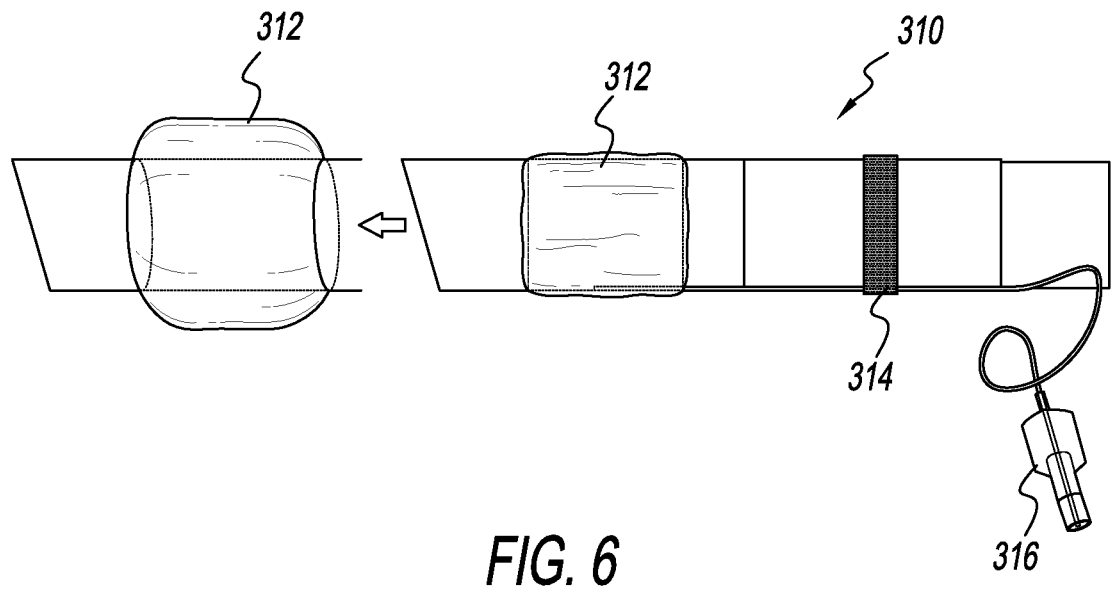
FIG. 6 is a side view of an inner tube in accordance with an embodiment of the invention.
Figure 7:
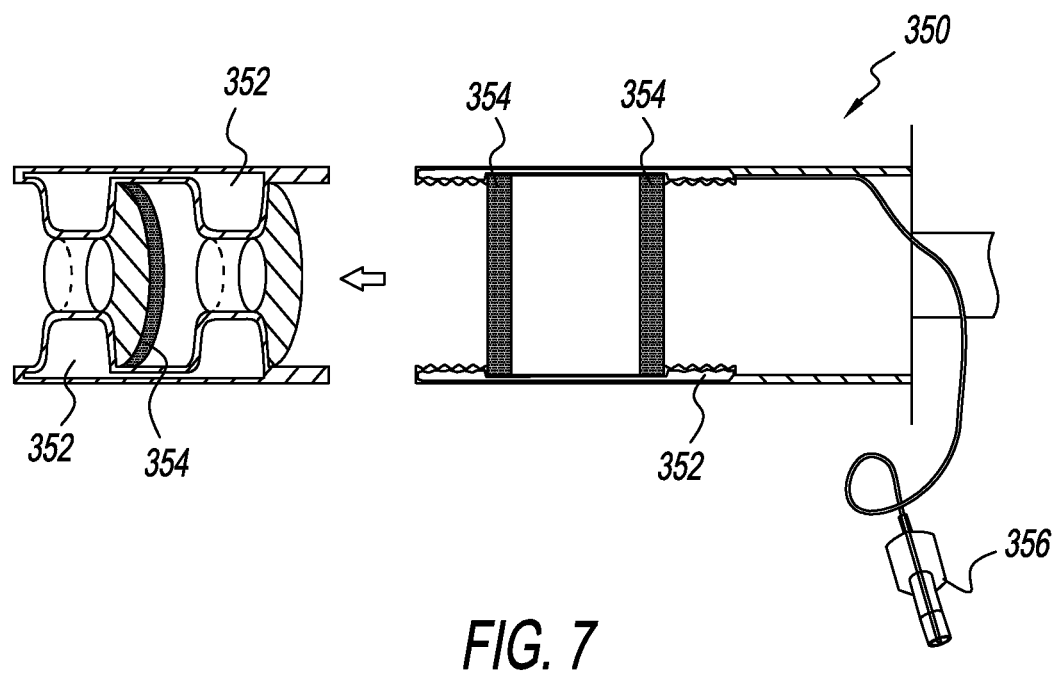
FIG. 7 is a side view of an outer tube in accordance with an embodiment of the invention.
Figure 8:
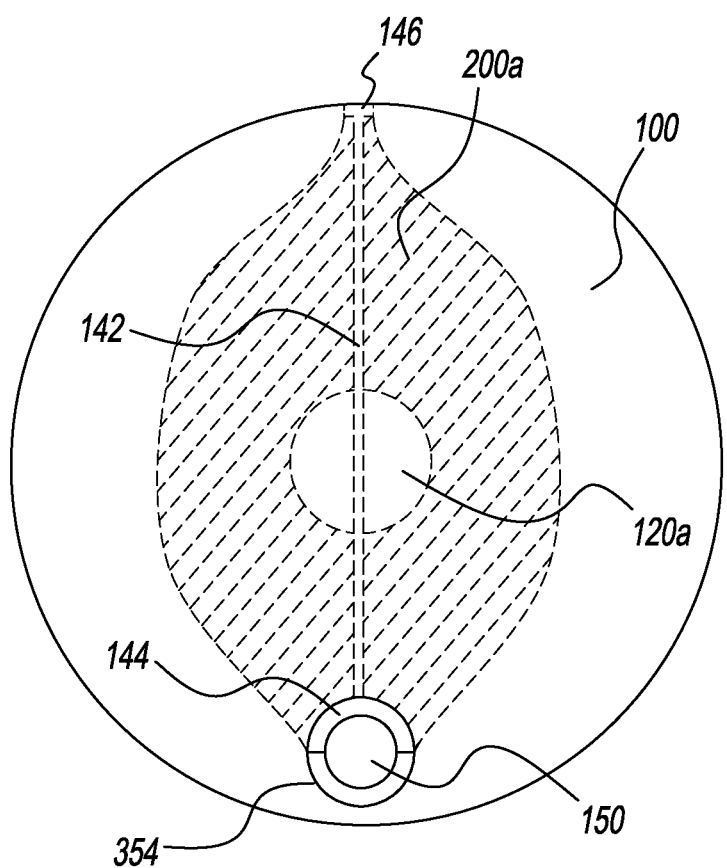
FIG. 8 is a top view of an ostomy pouching device in accordance with an embodiment of the invention.
Figure 9:
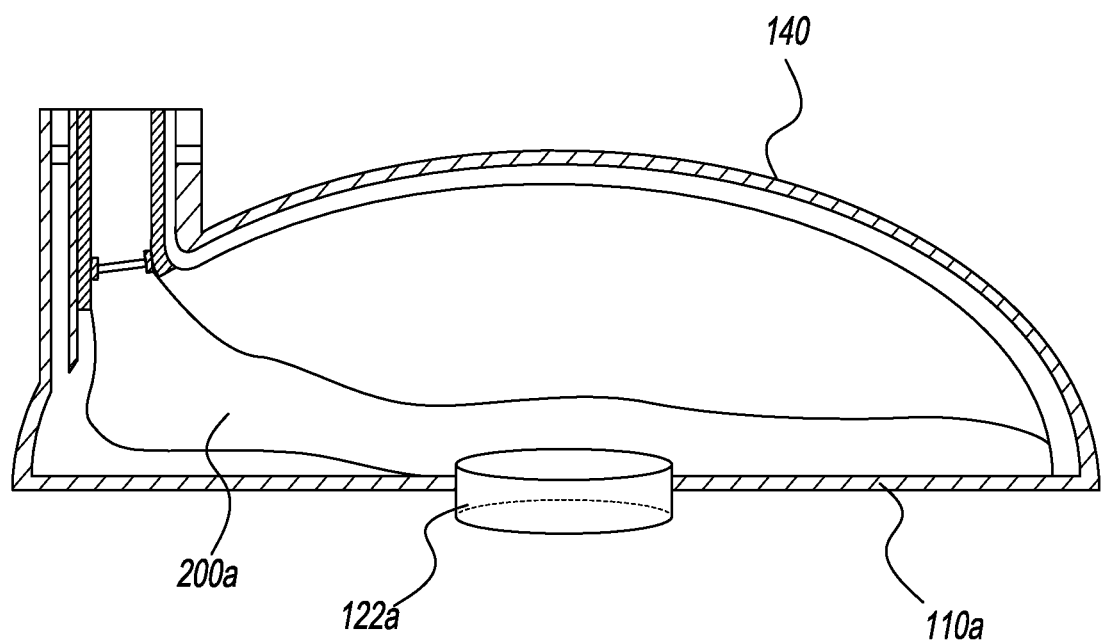
FIG. 9 is a side cross-sectional view of the device of FIG. 8.
Figure 10:
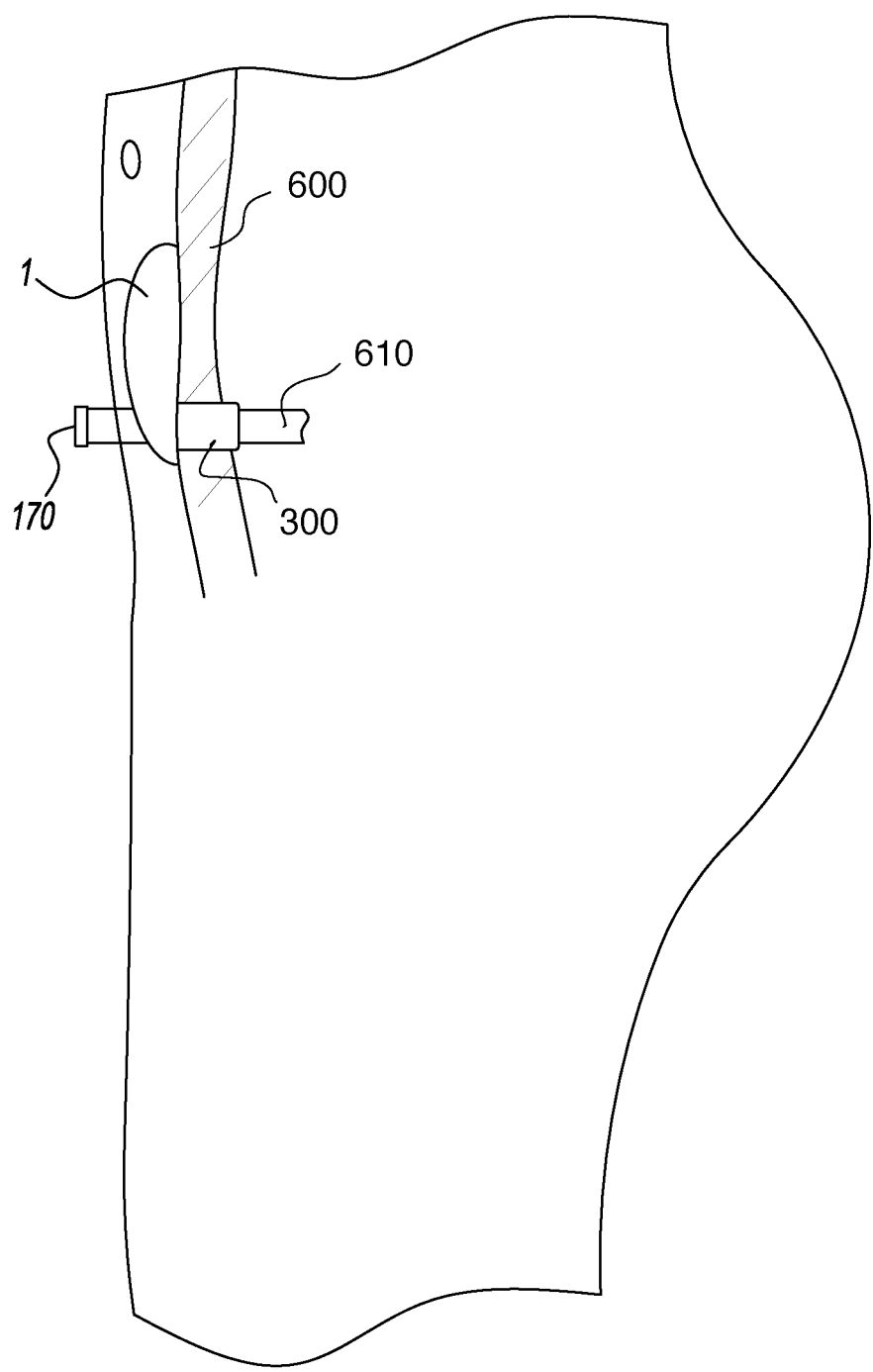
FIG. 10 is an illustration of an ostomy pouching device in accordance with an embodiment of the invention implanted into a human body.

Reference is made to the embodiment of bowel connector 300 shown in FIGS. 4-7. When in use, the end of the user's bowel is inserted into outer tube 350 and over inner tube 310, being sandwiched therebetween. Both inner tube 310 and outer tube 350 include one or more balloons for securing the bowel in place, as illustrated in FIG. 4. Inner tube 310 includes a cylindrical, donut-shaped inner tube balloon 312 on the exterior thereof as shown in FIG. 6, such that the outer diameter increases when the inner tube balloon 312 is inflated, thus exerting pressure on the bowel from the inside. Outer tube 350 includes two outer tube balloons 352 on the inside thereof, such that the inner diameter decreases when the outer tube balloons 352 are inflated as shown in FIG. 7. Thus, when the bowel is positioned between outer tube 350 and inner tube 310, the inner tube balloon 312 pushes outward onto the bowel and outer tube balloons 352 exert pressure inward onto the bowel. In the embodiment shown, tube balloons 352 are on either end of inner tube balloon 312 to prevent the displacement of inner tube 310. FIG. 4 illustrates bowel connector 300 having outer tube balloons 352 and inner tube balloon 312 inflated. In FIG. 5, outer tube balloons 352 are deflated, and thus inner tube 310 may be displaced. A pump 316, 356 may be provided for inflating inner tube balloon 312 and/or outer tube balloon 352 through a tube. The pump 316, 356 preferably extends through upper aperture 150 to the exterior of container 100 to permit the user to inflate the balloons. Preferably, pump 316, 356 may be used to deflate the balloons to facilitate removal of bowel connector 300 from the bowel.

Inner tube 310 and outer tube 350 shown also include biocompatible surfaces 314, 354 to permit human tissue to grow and bond thereto. Non-limiting examples include Polyethylene terephthalate and polytetrafluoroethylene (PTFE/Teflon). Biocompatible surface 314 of inner tube 310 is located on the outer surface of inner tube 310 to contact the inner surface of the bowel. Likewise, biocompatible surface 354 of outer tube 350 is located on the inner surface of outer tube 350 to contact the outer surface of the bowel. The biocompatible surface 314, 354 may contact the serosa and the sero-muscular edge of the ileostomy. During the healing process, the serosa may grow to adhere to the biocompatible surface 314, 354.

Figure 11:
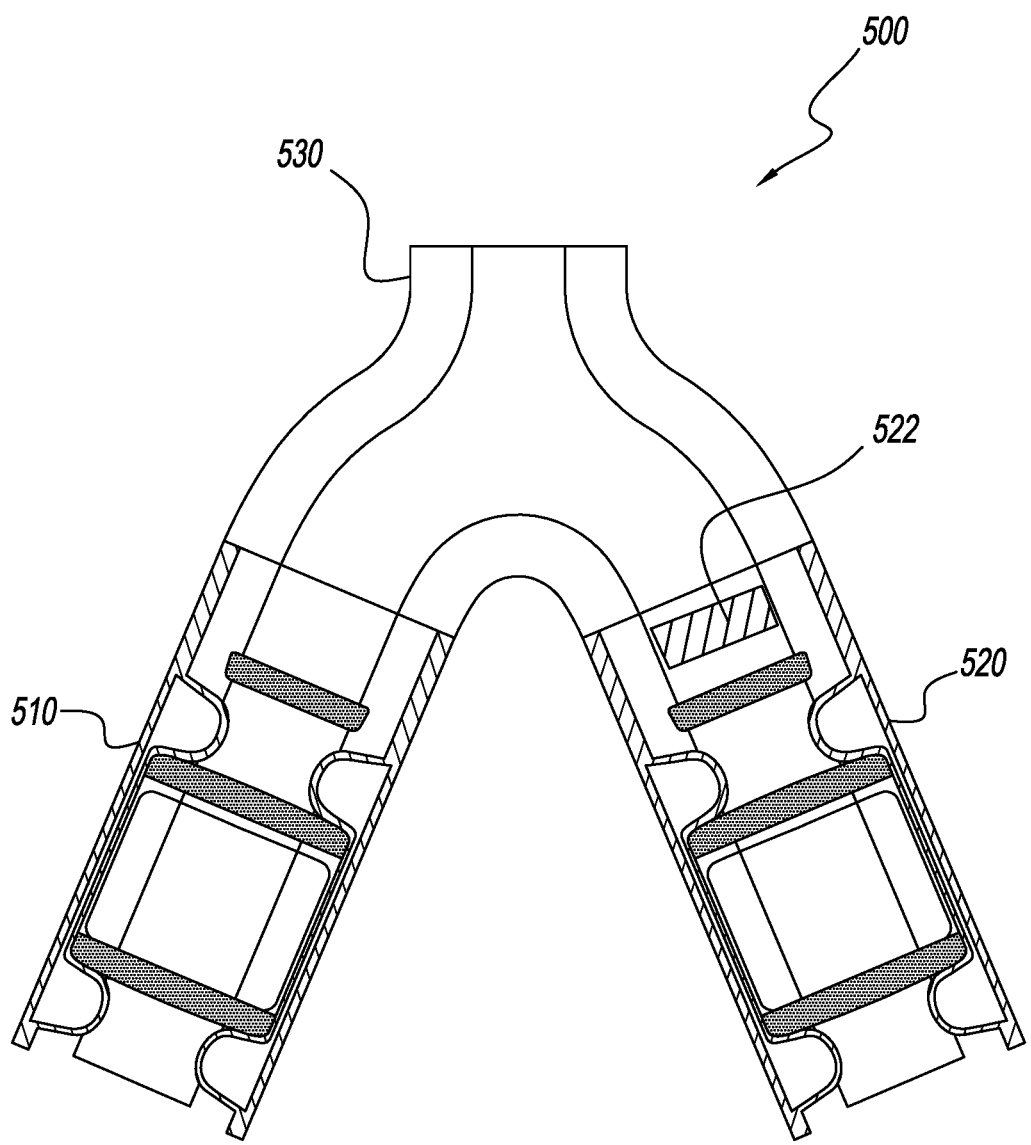
FIG. 11 is cross-sectional view of a bowel connector in accordance with an embodiment of the invention.

An alternate embodiment of a bowel connector 500 is illustrated in FIG. 11, wherein a Y-shape connector has three legs 510, 520, 530, each having an opening. First leg 510 connects to the upstream end of the user's bowel, second leg 520 connects to the downstream end of the bowel, and third leg 530 connects to the inner bag 200 and/or container 100. First leg 510 preferably includes an inner tube and outer tube, with a securing mechanism such as balloons as discussed with respect to the embodiment above. Second leg 520 may also include a similar inner tube and outer tube assembly. Preferably, second leg 520 further includes a stopper 522 to prevent content from the upstream end of the bowel entering first leg 510 from entering the downstream end of the bowel connected to second leg 520. More preferably, the legs include a control mechanism to open or close the opening of the respective leg. For example, when the device is implanted, the second leg 520's opening is closed, and the openings of first leg 510 and third leg 530 are open. Thus, content from the bowel enters the inner bag or container. After the user has received treatment for a few months, for example 3 to 6 months, or any other situation in which a temporary reconnection of the bowel is wanted, the opening of third leg 530 may be closed and the opening of second leg 520 is opened. Thus, content may flow from the upstream end of the bowel to the downstream end of the bowel. This reconnection may be desired to observe symptoms/issues of reconnection procedures, and allow various diagnostics, such as scopes, videos, etc., which may reduce the risk of issues after reconnecting the intestines.

An embodiment of device 1 also includes an external connector comprising external tube 410 and upper tunnel 152. External tube 410 connects to external connecting element 240 of inner bag 200, and extends through the inside of upper tunnel 152. The contents of inner bag 200 are removed through external tube 410. A cover 170 covers upper external tube 410, such that when cover 170 is removed, the contents of inner bag 200 or container 100 may be removed, preferably by applying pressure onto container 100. In accordance with an embodiment of the invention, cover 170 also covers upper tunnel 152 partially or entirely. In use, the user may remove cover 170 and press onto container 100, preferable displacing upper member 140 toward base 110, thus applying pressure onto the contents of container 100 and thus inner bag 200, pushing the contents through external tube 410. In accordance with an embodiment of the invention, cover 170 also covers gas exit 260.

The device 1 may include one or more sensors to detect the fullness, pressure, and/or weight of the inner bag 200 or container 100. A pressure sensor may sense the pressure in the gas tunnel 142. Another pressure sensor may measure the pressure within inner bag 200. Yet another sensor may measure the weight and fullness of inner bag 200. If container 100 receives the content from the bowel without an inner bag 200, one or more sensors may measure the pressure, weight, and/or fullness of container 100. One or more valves may be provided for the air exit aperture 154 and/or gas exit 144, and automatically released to relieve pressure in the container 100 or gas tunnel 142. Alternatively, the user may manually release the air or gas.

Preferably, inner bag 200 has a smaller volume than container 100. In accordance with an embodiment of the invention, container 100 has a length of between 5 to 20 cm, more preferably approximately 10 cm, the volume of container 100 is between 100 to 500 ml, more preferably between 200-300 ml. The thickness of container 100 may vary, for example, depending on the size of the user, whether it is implanted or attached externally. In accordance with a preferred embodiment, container 100 has a thickness of 15 cm or less, more preferably between 2 to 6 cm, when inner bag 200 is full.

Whereas the illustrated embodiments of container 100 have a generally round shape, it is to be understood that container 100 may have another shape without deviating from the scope of the invention. Preferably, container 100 lacks sharp or hard edges.

An embodiment of the invention provides a container into which content from the bowel enters the container without an inner bag therein. Bowel connector 300 connects directly to the base of the container. Preferably, the container expands as it is filled, and does not have substantive air that is displaced by the content. Alternatively, the air within the container may be displaced via the gas exit.

Figure 2:
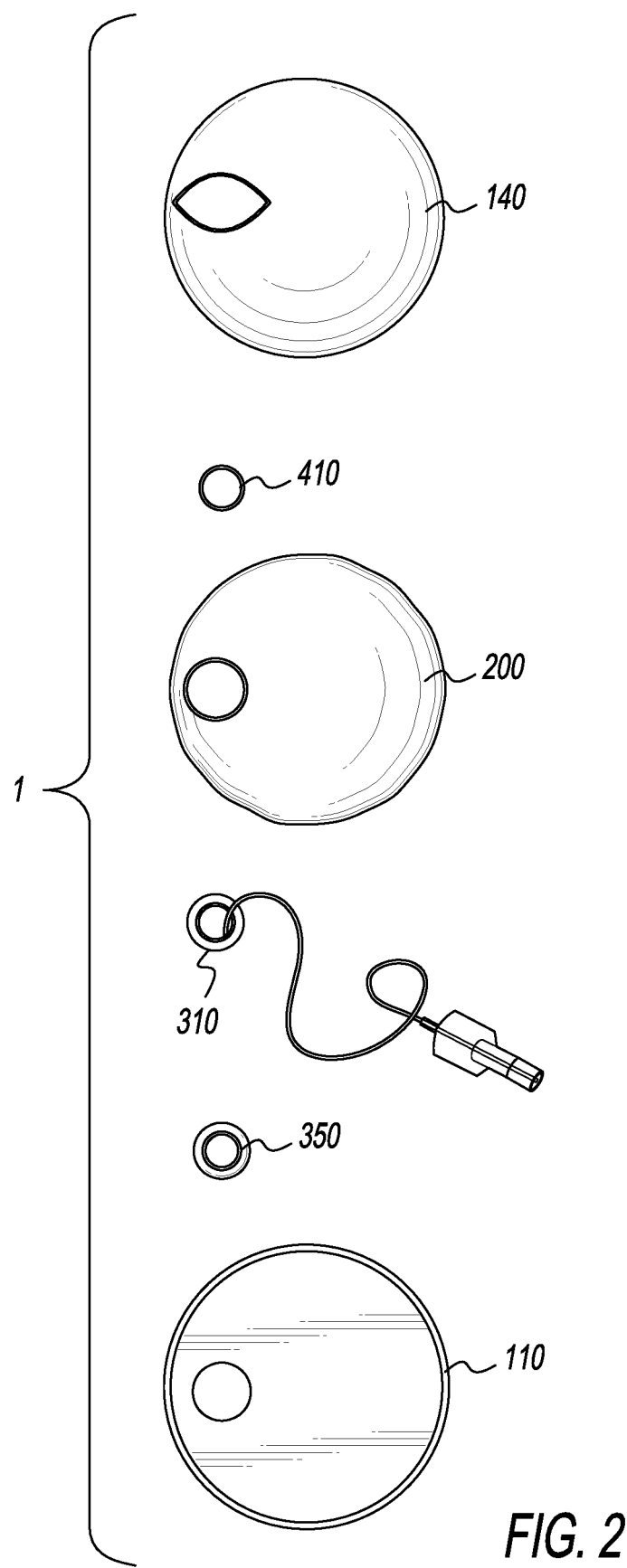
FIG. 2 is a top view of the components of FIG. 1.
Figure 3:
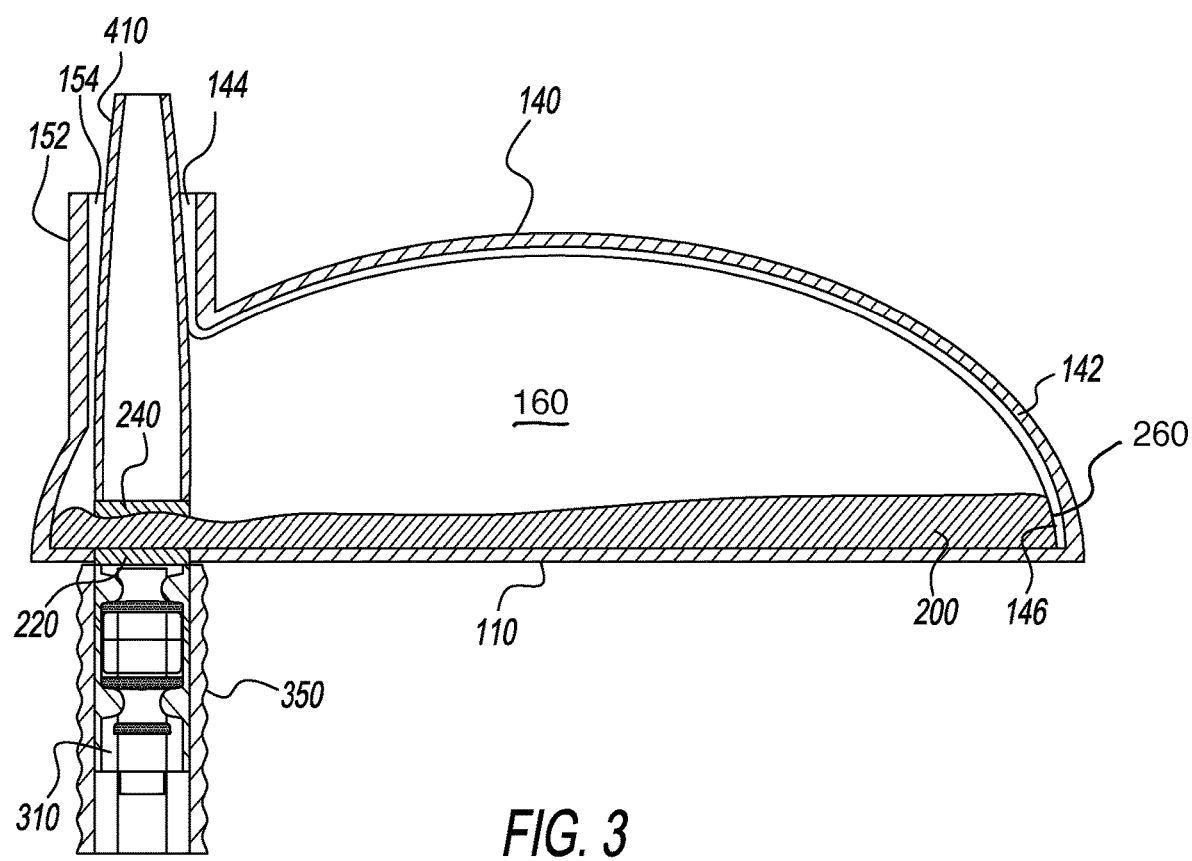
FIG. 3 is a side cross-sectional view of the device of FIG. 1.

Preferably, upper aperture 150 is aligned with or proximate base aperture 120 as shown in the embodiment illustrated in FIGS. 1-3. Such an arrangement may facilitate the removal/replacement of inner bag 200 or bowel connector 300, 500, troubleshooting issues with bowel connector 300, 500, adjusting the stopper 522, etc. In an alternative embodiment illustrated in FIGS. 8-9, upper aperture 150 is located lower than base tunnel 122a of base 110a when the patient using the device is standing. Likewise, the corresponding inner bag 200a has a bowel connection aligned with base tunnel 122a, and thus higher than upper aperture 150. Providing an upper aperture 150 lower than base tunnel 122a through which waste enters inner bag 200a may facilitate collecting waste in inner bag 200a with the assistance of gravity. It may also facilitate the removal of the waste from inner bag 200a.

Device 1 may be implanted inside the user's body, or it may be utilized externally and maintained outside of the body. In accordance with a preferred embodiment illustrated in FIG. 10, device 1 is implanted between the user's skin and abdominal muscle 600, and the outer wall surface of base 110 contacts the user's abdominal muscle. Bowel connector 300 extending into the body connects to the bowel 610 to receive waste therefrom.

Other alterations may be made without deviating from the scope of the invention. Accordingly, the device, the components thereof, and method of use, etc. may be varied as a matter of application specific design choice without deviating from the scope of the invention. For example, different mechanisms for securing the bowel to the container 100 and/or inner bag 200, positions of the upper aperture, base aperture, gas tunnel, gas exit, gas tunnel entrance, air exhaust etc. are contemplated. Whereas the illustrated embodiments provide the gas exit integrated with the upper aperture, a separate gas exit may be provided, for example, higher up on container 100 when the user is standing, with or without a gas tunnel. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall there between.

We claim:

1. An implantable ostomy device comprising:
   an outer shell made from implant stable material, comprising a proximal member and a distal member, sealed at their peripheries and together defining a first internal cavity, configured to be implanted between skin and abdominal muscles, said outer shell further comprising an external connector disposed on the proximal side, configured to traverse through subcutaneous tissues under the skin to connect the first internal cavity to the exterior of the skin adjacent the outer shell;
   a bowel connector configured to connect a patient's bowel to the internal cavity of the outer shell on the distal member, said bowel connector comprises at least one biocompatible surface; and
   an inner container defining a second internal cavity and disposed inside said outer shell in the first internal cavity, said inner container comprising an inner container entry aperture and an inner container exit aperture;
   a first connecting element positioned and connecting said inner container entry aperture to the bowel connector to allow the second cavity to receive contents from the bowel into the inner container through the bowel connector; and
   a second connecting element positioned and connecting said inner container exit aperture to the external connector of the outer shell to allow the contents in the second cavity to leave the inner container through the external connector to the outside of patient's body.

2. The device of claim 1, wherein said external connector further comprising a gas exit aperture.

3. The device of claim 1, further comprising one or more inflatable securing mechanisms.

4. The device of claim 1, wherein said inner container is a bag.

5. The device of claim 1, wherein said external connector is removably attached to the outer shell.

6. The device of claim 1, wherein the implant stable material is silicone.

7. The device of claim 1, wherein said inner container is removable through said external connector.

8. An implantable ostomy pouching device comprising:
   an outer container made from an implant stable material, the outer container comprising:
   a proximal first wall and a distal second wall, the first and second walls sealed at their peripheries and together defining a first cavity;
   a first entry aperture disposed on said proximal first wall and a first exit aperture disposed on said distal second wall, wherein the first entry aperture and the first exit aperture are substantially smaller than the first cavity;
   a bowel connector attached to the first entry aperture and configured to connect a patient's bowel as a stoma to the outer container at the first entry aperture of said outer container;
   an inner bag defining a second cavity and disposed inside said outer container in the first cavity, said inner bag comprising:
   a second entry aperture connected to said bowel connector adjacent said first entry aperture and a second exit aperture; wherein said inner bag positioned and configured to receive contents from the bowel through the bowel connector into the second cavity; and
   an exit tunnel member connected to the second exit aperture having a tunnel entrance aperture adjacent the second exit aperture and a tunnel exit aperture distal to the second exit aperture, said exit tunnel member is configured to traverse through subcutaneous tissues under the patient's skin extending from said tunnel entrance aperture through the first exit aperture of the outer container to the tunnel exit aperture outside the patient's body.

9. The device of claim 8, wherein the first entry aperture and the first exit aperture are aligned.

10. The device of claim 8, wherein the lumen of said exit tunnel is substantially smaller than the cavity of said container.

11. The device of claim 8, wherein first wall and said second wall are asymmetrically shaped.

12. The device of claim 8, further comprising a gas tunnel having a gas entrance and a gas exit.

13. The device of claim 12, wherein gas within said inner bag enters said gas tunnel through said gas entrance and exits said device through said gas exit.

14. The device of claim 12, wherein gas within said container enters said gas tunnel through said gas entrance and exits said device through said gas exit.

15. The device of claim 12, further comprising a valve at said gas exit adapted to releasing gas from within said gas tunnel.

16. The device of claim 8, wherein said container includes an air exit aperture through which air within said container exits said container.

17. The device of claim 8, wherein said exit tunnel is removably attached to the container.

18. The device of claim 8, wherein the first entry aperture and the first exit aperture are not aligned.

19. The device of claim 18, wherein the first entry aperture is positioned vertically higher than the first exit aperture.

20. The device of claim 8, wherein said exit tunnel further comprising a cover.

21. The device of claim 8, wherein said container includes a gas tunnel within a container wall.

22. The device of claim 8, further comprising a plurality of gas tunnels.

23. The device of claim 5, wherein said inner bag is removable through said exit tunnel.

24. The device of claim 8, wherein said inner bag is made of a gas permeable material.

25. An implantable ostomy device comprising:
- an implantable outer container made from implant stable material configured to be implanted in subcutaneous tissues between the skin and the abdominal muscle of a patient, said implantable container comprising a skin-facing upper member and a muscle-facing base member, the upper member, having a upper member aperture and the base member having a base member aperture, are sealed at their peripheries and together defining a first internal cavity;
- an exit chimney configured to extend from the upper member aperture of the upper member through subcutaneous tissues to the exterior of the skin adjacent the implantable outer container;
- a bowel connector configured to connect to a bowel of a user as a stoma to the base member said implantable outer container at the base member aperture;
- collapsible inner container having a second cavity and disposed inside said implantable outer container in the first internal cavity, said inner container having an inner container entry aperture positioned adjacent the base member aperture of the implantable outer container, configured to allow the second cavity of the inner container to receive contents from the bowel through the stoma and through the bowel connector, and an inner container exit aperture positioned adjacent the upper member aperture to allow contents from the inner container to exit the second cavity through the inner container exit aperture, the upper member aperture and through the exit chimney to the outside of the patient's body; and
- wherein the upper member aperture and base member aperture are substantially smaller than the first cavity;
- wherein the inner container entry aperture and the inner container exit aperture are substantially smaller than the second cavity.

26. The device of claim 25, wherein the inner container is an inflatable bag.

27. The device of claim 25, wherein the skin-facing upper member is dome shaped.

28. The device of claim 25, wherein the muscle-facing base member is substantially flat.

29. The device of claim 25, wherein said upper member is flexible.

30. The device of claim 25 wherein the lumen of the exit tunnel is substantially smaller than the cavity of said outer container.

31. The device of claim 25, wherein the inner container is removably attached to the outer container.

32. The device of claim 25 wherein the exit tunnel and the bowel connector are vertically aligned.

33. An ostomy pouching device comprising:
- an implantable container constructed from material stable as an implant configured to be implanted in a patient's abdomen between the patient's skin and abdominal muscles, said implant container comprising a curved upper member having a first aperture and a substantially flat lower member having a second aperture, said upper member and lower member are sealed at their peripheries and together defining an internal cavity capable of holding and storing content;
- wherein said lower member further comprises a bowel connector attached to the second aperture and configured to connect a patient's bowel as a stoma to implantable container at the second aperture of said container;
- wherein said upper member further comprises an exit tunnel connected to the first aperture having a tunnel entrance aperture adjacent the first aperture and a tunnel exit aperture distal to the first aperture, said exit tunnel is configured to traverse subcutaneous tissues under the patient's skin extending from said tunnel entrance aperture to the tunnel exit aperture, thereby allowing content in the internal cavity to leave the container throught the exit tunnel to outside the patient's body;
- wherein said internal cavity is substantially larger than the lumen of said exit tunnel; and
- wherein said first and second apertures are substantially smaller than the internal cavity.

34. A method of creating a stoma inside a patient's body comprising:
- placing an implantable ostomy pouching device according to claim 5 between the patient's skin and abdominal muscle; and
- attaching a portion of a bowel of said patient to said bowel connector of the implantable ostomy pouching device.

35. A method of replacing an inner bag in a container implanted in a patient's body, said method comprising:
- removing an inner bag from an implantable ostomy pouching device according to claim 5 through the exit tunnel of said implantable container;
- inserting a new inner bag into said implantable container; and
- securing said inner bag to to said implantable container.

36. A method of reconnecting a severed bowel comprising;
- providing an implantable ostomy device of claim 1, wherein the bowel connector further comprises an upstream leg connected to an upstream end of a bowel, a downstream leg connected to a downstream end of a bowel, and an ostomy leg connected to the ostomy device;
- removing a first stopper from said downstream leg; and
- placing an ostomy stopper within said ostomy leg;
- wherein once said first stopper is removed and said ostomy stopper is placed within said ostomy leg, waste matter can travel from said upstream end of a bowel to said downstream end of a bowel.

37. A method of implanting an ostomy device in a patient comprising:
- placing an implantable ostomy pouching device according to claim 33 between the patient's skin and abdominal muscle; and
- attaching a portion of a bowel of said patient to said bowel connector of the ostomy pouching device.

* * * * *